(12) United States Patent
Thalgott

(10) Patent No.: US 6,558,424 B2
(45) Date of Patent: May 6, 2003

(54) MODULAR ANATOMIC FUSION DEVICE

(75) Inventor: John S. Thalgott, Las Vegas, NV (US)

(73) Assignee: DePuy Acromed, Raynham, MA (US)

( * ) Notice: Subject to any disclaimer, the term of this patent is extended or adjusted under 35 U.S.C. 154(b) by 0 days.

(21) Appl. No.: 09/894,315

(22) Filed: Jun. 28, 2001

(65) Prior Publication Data

US 2003/0004576 A1 Jan. 2, 2003

(51) Int. Cl.⁷ .................................................. A61F 2/44
(52) U.S. Cl. ................................ 623/17.16; 623/17.11
(58) Field of Search ........................... 623/17.11, 17.15, 623/17.16; 606/61

(56) References Cited

U.S. PATENT DOCUMENTS

| | | | |
|---|---|---|---|
| 4,759,769 A | | 7/1988 | Hedman et al. |
| 5,071,437 A | | 12/1991 | Steffee |
| 5,192,327 A | * | 3/1993 | Brantigan ..................... 623/17 |
| 5,245,098 A | | 9/1993 | Summers et al. |
| 5,246,458 A | | 9/1993 | Graham |
| 5,306,309 A | | 4/1994 | Wagner et al. |
| 5,397,364 A | | 3/1995 | Kozak et al. .................. 623/17 |
| 5,425,772 A | * | 6/1995 | Brantigan ..................... 623/17 |
| 5,429,863 A | | 7/1995 | McMillin |
| 5,458,643 A | | 10/1995 | Oka et al. |
| 5,514,180 A | | 5/1996 | Heggeness et al. |
| 5,534,030 A | | 7/1996 | Navarro et al. |
| 5,571,109 A | | 11/1996 | Bertagnoli |
| 5,674,294 A | | 10/1997 | Bainville et al. |
| 5,683,465 A | | 11/1997 | Shinn et al. |
| 5,741,253 A | | 4/1998 | Michelson |
| 5,776,196 A | | 7/1998 | Matsuzaki et al. |
| 5,824,094 A | | 10/1998 | Serhan et al. |
| 5,865,846 A | | 2/1999 | Bryan et al. |
| 5,893,889 A | | 4/1999 | Harrington |
| 6,033,438 A | | 3/2000 | Bianchi et al. ................ 623/17 |
| 6,090,143 A | * | 7/2000 | Meriwether ................... 623/17 |
| 6,110,210 A | | 8/2000 | Norton et al. ............. 623/17.16 |
| 6,129,763 A | * | 10/2000 | Chauvin et al. ............... 623/17 |
| 6,159,211 A | * | 12/2000 | Boriani et al. ................. 606/61 |
| 6,224,631 B1 | * | 5/2001 | Kohrs ....................... 623/17.11 |
| 6,258,125 B1 | | 7/2001 | Paul et al. |
| 6,261,586 B1 | | 7/2001 | McKay |
| 6,270,528 B1 | | 8/2001 | McKay |
| 6,290,724 B1 | * | 9/2001 | Marino ..................... 623/17.11 |
| 6,458,159 B1 | * | 10/2002 | Thalgott .................... 623/17.11 |
| 6,468,311 B2 | * | 10/2002 | Boyd et al. ............... 623/17.16 |

(List continued on next page.)

FOREIGN PATENT DOCUMENTS

| | | |
|---|---|---|
| WO | WO 01/49220 | 7/2001 |
| WO | WO 01/62191 | 8/2001 |
| WO | WO 01/66048 | 9/2001 |
| WO | WO 01/70137 | 9/2001 |
| WO | WO 01/78798 | 10/2001 |

OTHER PUBLICATIONS

*Surgical Technique Using FRA Spacer Instruments: Technique Guide*, Synthes Spine, pp. 1–16 (1998).
*Keystone Graft Instruments*, Pamphlet by DePuy Motech, Inc., 6 pages (1998).

Primary Examiner—Ralph A. Lewis
(74) Attorney, Agent, or Firm—Nutter, McClennen & Fish LLP

(57) ABSTRACT

A modular fusion cage and tool for the insertion of the fusion cage is provided. The fusion cage includes a ramp member having superior and inferior bone contacting surfaces, and anterior and posterior sides. The ramp member is adapted to be positioned between adjacent vertebral bodies. The implant also includes a ring member slidably matable with the ramp member. The ring member includes superior and inferior bone contacting surfaces, and anterior and posterior sides. The implant according to the present invention is particularly useful for facilitating the safe and accurate insertion of the implant between adjacent vertebral bodies.

43 Claims, 10 Drawing Sheets

U.S. PATENT DOCUMENTS

2001/0039456 A1   11/2001   Boyer, II et al.
2001/0039457 A1   11/2001   Boyer, II et al.
2001/0039458 A1   11/2001   Boyer, II et al.
2001/0041941 A1   11/2001   Boyer, II et al.
2001/0047208 A1   11/2001   Michelson
2001/0049560 A1   12/2001   Paul et al.
2001/0056302 A1   12/2001   Boyer, II et al.
2002/0029084 A1    3/2002   Paul et al.

* cited by examiner

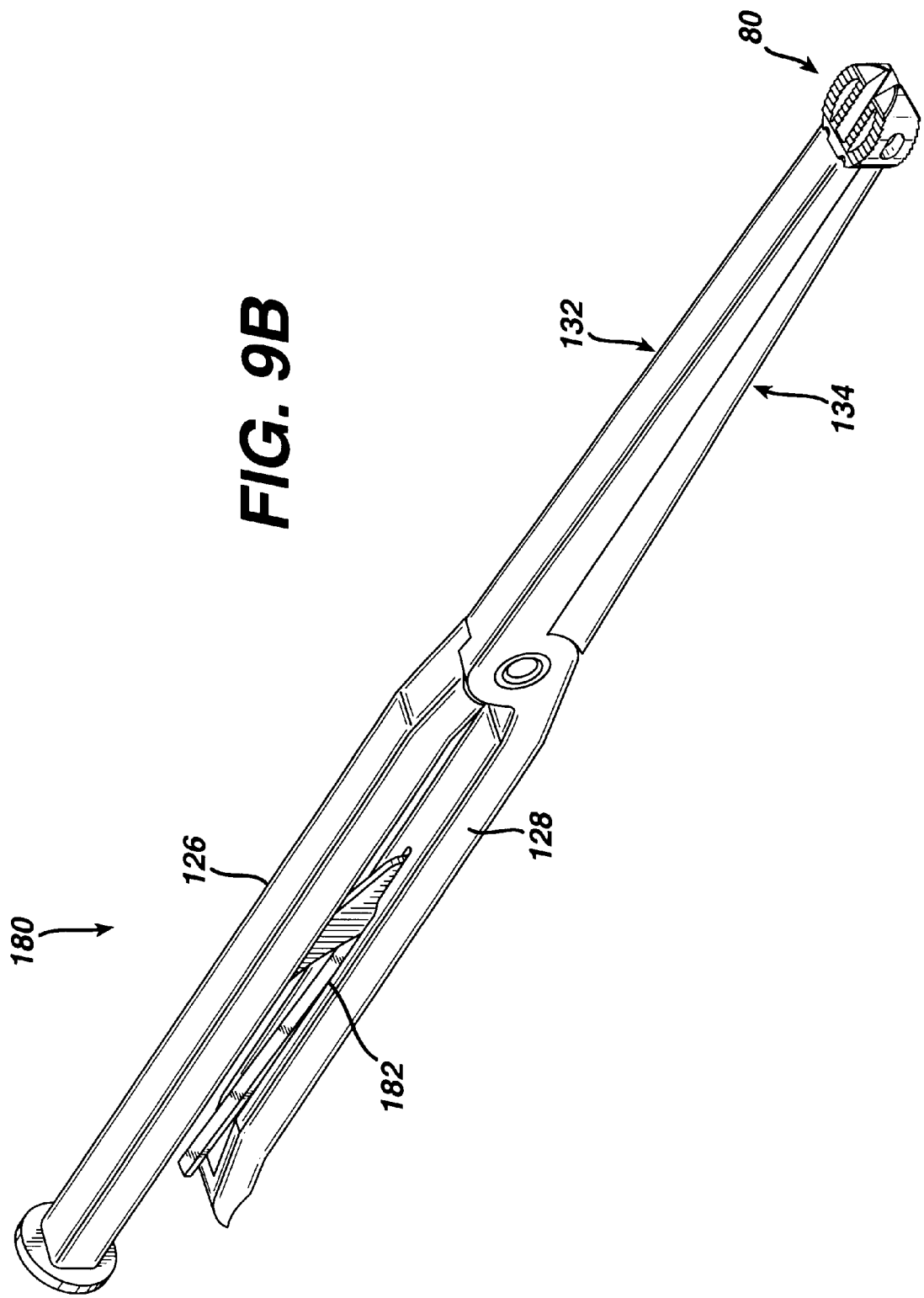

MODULAR ANATOMIC FUSION DEVICE

FIELD OF THE INVENTION

The present invention relates to spinal implants, tools for the insertion of spinal implants, and methods of use thereof, and more particularly, to an implantable modular fusion cage for promoting fusion of adjacent vertebral bodies.

BACKGROUND OF THE INVENTION

Degenerative changes in the spine can cause the loss of normal structure and/or function. The intervertebral disk is one structure prone to the degenerative changes associated with wear and tear, aging, and even misuse. Over time the collagen (protein) structure of the intervertebral disk weakens and may become structurally unsound. Additionally, the water and proteoglycan (the molecules that attract water) content decreases, thereby narrowing the space between the adjacent vertebrae, which can result in nerve root compression and pain. These changes can lead to the disk's inability to handle mechanical stress.

One form of treatment available for degenerative disk disease is spinal fusion surgery, which involves the surgical removal of a portion or all of an intervertebral disk followed by fusion of the adjacent vertebrae. A prosthetic device, e.g. a fusion cage, is usually placed between the two adjacent vertebrae to fill the space left by the removed disk and to allow bone to grow between the adjacent vertebrae.

Spinal fusion procedures can present the surgeon with several challenges, especially where the disk is severely degenerative. When the natural disk is removed, the adjacent vertebral bodies collapse upon each other thereby requiring the bodies to be separated to enable placement of the prosthesis. However, separation or distraction of the vertebral bodies beyond a certain degree can result in further injury or damage to the vertebrae. Conversely, where the disk is severely degenerative, the narrow disk space and lack of elasticity between the vertebrae can hinder the surgeon's ability to separate the vertebrae to a height sufficient to enable placement of the prosthesis.

To overcome some of these problems, specialized tools have been developed to facilitate the placement of disk prosthesis between adjacent vertebral bodies of a patient's spine. Among the known tools for performing such procedures are spinal distracters, e.g. spreaders, and insertion devices. In general, the spreader is placed between adjacent vertebrae, and then used to pry the vertebrae apart. Once the space between the vertebral bodies is sufficient to enable placement of a prostheses, the prosthetic device can then be inserted, either manually or with an insertion tool, into the space to hold the adjacent vertebrae apart. Typically, cancellous bone is packed in and/or around the cage to promote fusion of the adjacent vertebrae.

While most spreader devices are effective to assist surgeons with the placement of disk prosthesis, the use of such tools can prove cumbersome. For example, insertion of a spreader device into the limited disk space can cause fracture of a vertebra. Moreover, once inserted, the spreaders can cause over-distraction of the vertebral bodies, or can hinder placement of the prosthesis. In the presence of degenerative disease or chronic changes where the disk space has become narrow, it can be difficult to maintain an adequate interbody height and, at the same time, insert and position the implant. Over-insertion, or under-insertion of the prosthesis can lead to pain, postural problems and/or limited mobility or freedom of movement.

Despite existing tools and technologies, there remains a need for a device to facilitate the safe and accurate insertion of a disk prosthesis between adjacent vertebral bodies while minimizing the risk of further injury to the patient.

SUMMARY OF THE INVENTION

The present invention provides a modular fusion cage for promoting fusion of adjacent vertebral bodies, and a tool for the insertion of the fusion cage. The implant is effective for maintaining an adequate interbody height between adjacent vertebrae during insertion, and therefore is particularly useful for patients with degenerative disk disease. In addition, the modularity of the implant facilitates the safe and accurate insertion of the implant between adjacent vertebrae. The modular fusion cage of the invention is particularly useful as an anterior fusion cage.

In general, the modular fusion cage includes a ramp member and a ring member, each of which has superior and inferior bone contacting surfaces, and anterior and posterior sides. The ramp member is adapted to be positioned between adjacent vertebral bodies, and the ring member is slidably matable with the ramp member.

In one embodiment, the ring member is generally C-shaped with an opening that is preferably disposed on the posterior side of the ring member. The opening represents an interruption in the continuity of the annular walls of the ring member and is effective for receiving the ramp member. The ring member can also include a substantially wedge-like posterior tip formed between the superior and inferior surfaces of the ring. The ramp member can include transverse sides connecting the superior and inferior surfaces, each of which can be adapted to conform to the opening in the ring member.

In one embodiment, the ring member further includes first and second rib structures that extend substantially parallel to each other between the posterior and anterior sides of the ring member. The first and second rib structures are each separated from the side walls of the ring member, and each other, by openings in which bone growth promoting materials, e.g. cancellous bone, can be placed.

The superior and inferior surfaces of the ring and/or ramp members of the modular fusion cage of the present invention can have any shape, and can include bone engaging surface features (e.g. teeth or ridges) formed on at least a portion thereof. Preferably, these surfaces are generally shaped and contoured to conform to and to be complimentary to the surfaces of the vertebral bodies that they are intended to contact. By way of non-limiting example, the superior and inferior surfaces of the ring and/or ramp members can have a convex shape, or can have a height extending between the superior and inferior surfaces that is greater at the anterior side than at the posterior side of the ring/ramp member.

As a modular fusion cage, the components that form the cage are assembled within the patient's body during a surgical procedure. The ramp member is positioned first and the ring member is subsequently installed and mated to the ramp member. To ensure proper mating, the ring and/or ramp members include alignment features that assist in aligning the ring member with the ramp member during insertion. The alignment guide can be, for example, a tongue and groove formed on the transverse side walls of the ramp member and the opening in the ring member. The ring and ramp members can optionally include other features, such as a locking mechanism effective to lock the ring and ramp members together, or a handle removably attached to the ramp member for inserting the ramp member into the disk space, and optionally for inserting the ring member around the ramp member.

In yet another embodiment, a spinal implant system is provided having a modular fusion cage and an insertion tool for implanting the modular cage within the vertebral disk space. The modular fusion cage includes a ramp member and a ring member, each having posterior and anterior faces, and superior and inferior bone contacting faces. The posterior face of the ring member defines an opening for receiving the ramp member, and the anterior side of the superior and inferior faces each have at least one groove formed therein for receiving the insertion tool. The insertion tool includes first and second opposed grasping elements movable between an open position and a closed position, and matable with the at least one groove formed in each of the superior and inferior surfaces of the ring member. First and second opposed actuating members are mated to the first and second grasping elements and are effective to move the first and second grasping elements between the open and closed positions.

BRIEF DESCRIPTION OF THE DRAWINGS

The invention will be more fully understood from the following detailed description taken in conjunction with the accompanying drawings, in which:

FIG. 9B is a top perspective view of another embodiment of an insertion tool according to the present invention.

DETAILED DESCRIPTION OF THE INVENTION

The present invention provides an implantable modular fusion cage that is effective to fuse together adjacent vertebral bodies. The modular fusion cage of the present invention is particularly useful for patients with degenerative disk disease, where the deteriorated elasticity between adjacent vertebral bodies causes the bodies to collapse. The modular fusion cage is effective to maintain an adequate interbody height between adjacent vertebrae during insertion of the remainder of the implant, and thereby eliminates the necessity for additional tools to overcome the deteriorated elasticity between the vertebrae. The fusion cage is also effective to provide greater flexibility in implantation and assists with alignment of the cage between adjacent vertebrae. A tool for inserting the modular fusion cage according to the present invention is also provided.

Figure 1:
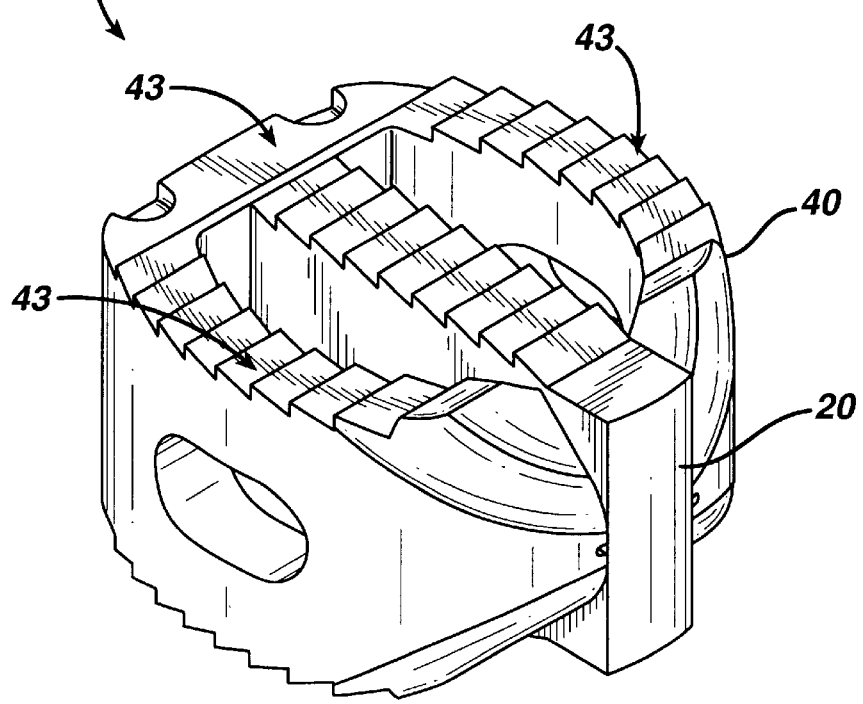
FIG. 1 is a posterior perspective view an implantable modular fusion cage having a ring member and a ramp member according to one embodiment of the present invention.
Figure 2:
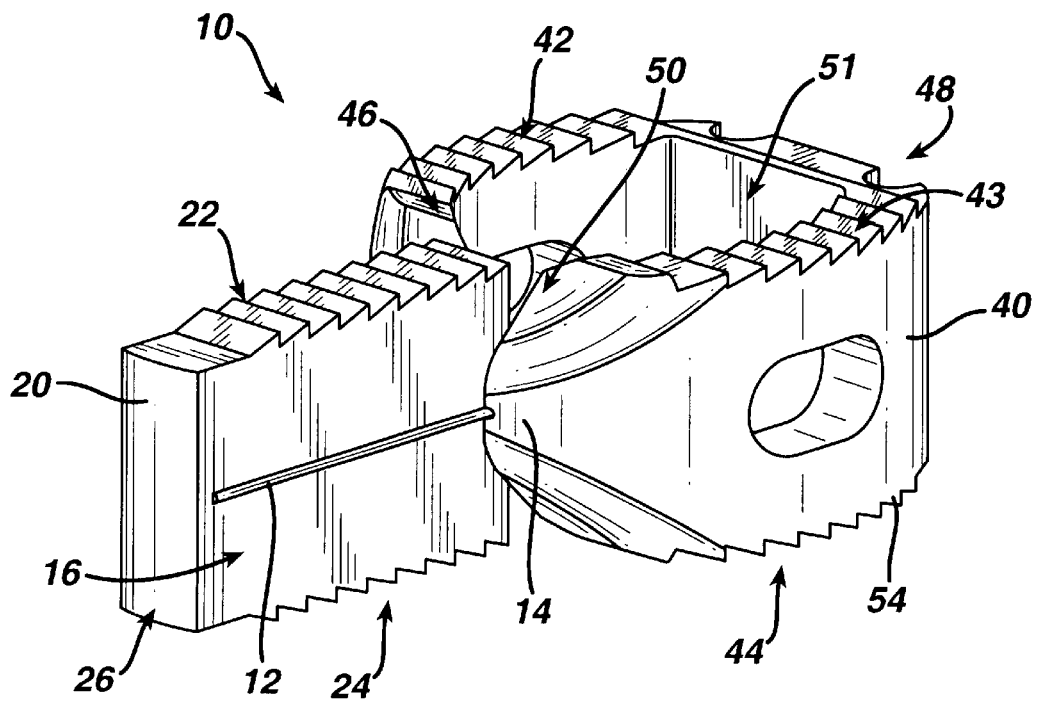
FIG. 2 is another posterior perspective view of the modular fusion cage shown in FIG. 1, in a partially assembled condition.

Referring to FIGS. 1 and 2, the modular fusion cage 10 according to the present invention generally includes two modular components: a ramp member 20 and a ring member 40. The modular fusion cage 10 has a size and a geometry that enables it to be efficiently installed and to remain securely positioned between adjacent vertebral bodies until healing and fusion take place.

The ramp member 20 has superior and inferior bone-contacting surfaces 22, 24, posterior and anterior sides 26, 28, and first and second transverse sides 32, 34, respectively. Similarly, the ring member 40, which is formed by an annular wall 43, has superior and inferior bone contacting surfaces 42, 44, posterior and anterior sides 46, 48, and opposed transverse sides 52, 54. The annular wall 43 is interrupted by a wall opening 50 that gives the ring member a substantially C-like shape. Preferably, the wall opening 50 is formed in a posterior side of the annular wall. The annular wall 43 also defines a central opening 51 that is oriented in the superior-inferior plane, and communicates with the wall opening 50.

The wall opening 50 is dimensioned to accept the ramp member 20, which fits within the central opening 51 in the course of mating with the ring member 40. Use of the ramp member 20 is effective to hold adjacent vertebrae apart while the ring member 40 is slidably inserted around the ramp member 20, and thereby obviates the need for a spreader tool during a fusion procedure.

Figure 3A:
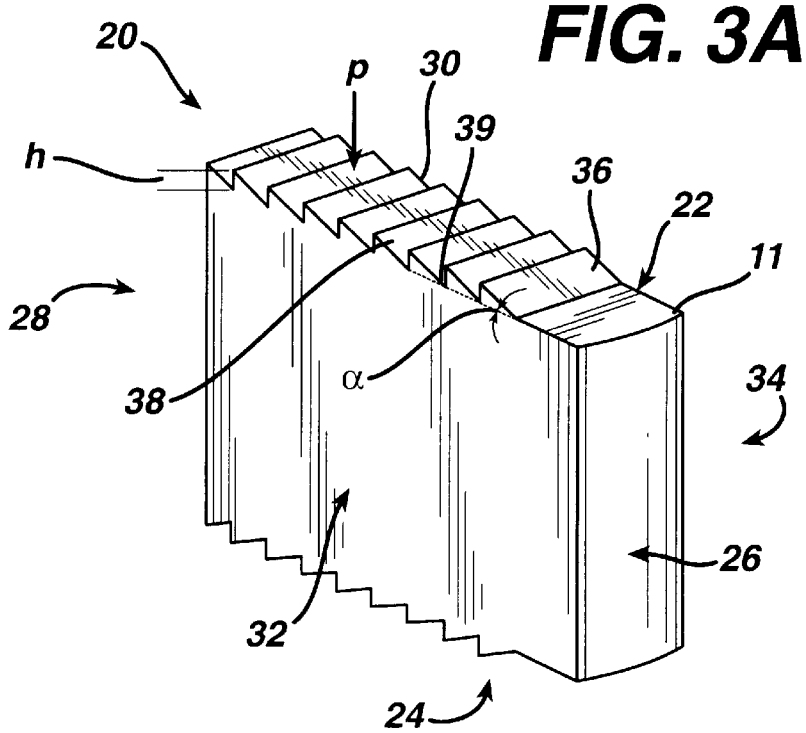
FIG. 3A is a posterior perspective view of a ramp member according to one embodiment of the present invention.

FIG. 3A illustrates one embodiment of the ramp member 20 having a generally rectangular shape and including superior and inferior bone-contacting surfaces 22, 24, posterior and anterior sides 26, 28, and first and second transverse sides 32, 34. The ramp member 20 can have any shape and size, but should have a height and width sufficient to fit within the vertebral space. The size of the ramp member 20 can vary depending upon a variety of factors, including the size of the ring member 40 and the objectives relating to use of the modular fusion cage 10. Preferably, the height of the ramp member 20 is equal to or greater than the height of the ring member 40 to provide a vertebral opening in which the ring member 40 can be placed. The superior and inferior surfaces 22, 24 of the ramp member 20 can be parallel to one another, as shown in FIG. 3A, or, as described below, the ramp member 20 can have a somewhat wedge-like shape, or it can be shaped to match the end plates of the adjacent vertebrae.

Figure 3B:
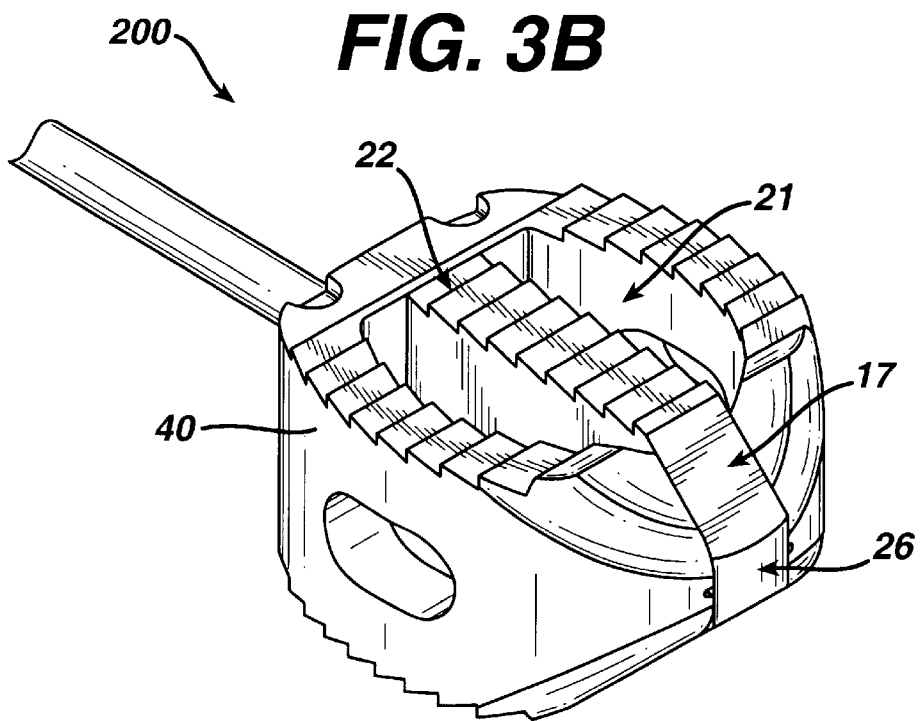
FIG. 3B is a posterior perspective view of another embodiment of a ramp member mated to a ring member according to the present invention.

FIG. 3B illustrates another embodiment of a ramp member 21 having a height equal to the height of the ring member along the entire superior and inferior surfaces 22, 24. As shown, the ramp member 21 includes converging surfaces 17 formed along the posterior side 26 to facilitate the insertion of the ramp member 21 between adjacent vertebrae. Preferably, the converging surfaces 17 are formed by a general incline or curvature of the opposed superior and inferior surfaces 22, 24 towards each other. The converging surfaces 17 can extend over a region that represents a distance of about 10 to 50 percent of the anterior-posterior depth of the ramp member 21, and can have an angle of convergence between about 10 and 25 degrees, and most preferably about 17.5 degrees. As illustrated, the posterior side 26 of the ramp member can have a generally rounded shape.

The ramp member 20 can optionally include a number of bone engaging surface features 34 formed on the superior and inferior surfaces 22, 24 to facilitate the secure mounting of the ramp member 20 between the vertebral bodies. The bone engaging surface features can be present on the entire surface area of the superior and inferior surfaces 22, 24, or optionally, selected regions of the superior and inferior surfaces 22, 24 can be free of surfaces features 30. As shown in FIG. 3A, the posterior region of the superior and inferior surfaces 22, 24 is free of bone engaging surface features to facilitate the insertion of the implant from an anterior or anterior-lateral surgical approach.

The bone engaging surface features 30 can have a variety of shapes, but are preferably in the form of wedge-shaped ridges formed on the superior and inferior surfaces 22, 24 and extending between the transverse sides 32, 34 of the ramp member 20. Each bone engaging surface feature 30 includes a posterior side wall 36 and an anterior side wall 38, which meet at a peak p. Preferably, the posterior side wall 36 of each bone engaging surface feature 30 slopes downwardly toward the posterior side 26 of the ramp member 20 to facilitate insertion of the ramp member 20 into the disk space. The posterior side wall 36 may be sloped at an angle ($\alpha$) with respect to the base 39 of superior or inferior surface 22, 24 of the ramp member 20. The value of the angle ($\alpha$) is preferably in the range of about 5° to 60°.

The bone engaging surface features 30 should have a size sufficient to cause each surface to engage and penetrate the adjacent vertebrae. Preferably, each surface feature has a height h, which can be in the range of about 0.5 to 2.5 mm, and more preferably is about 0.75 mm, as measured from the superior or inferior surface 22, 24. It will be understood that while ridges have been shown in a preferred embodiment, it is contemplated that there are a variety of structures which could provide a surface for effective engagement with the vertebral bodies to limit expulsion from the disc space.

Figure 4A:
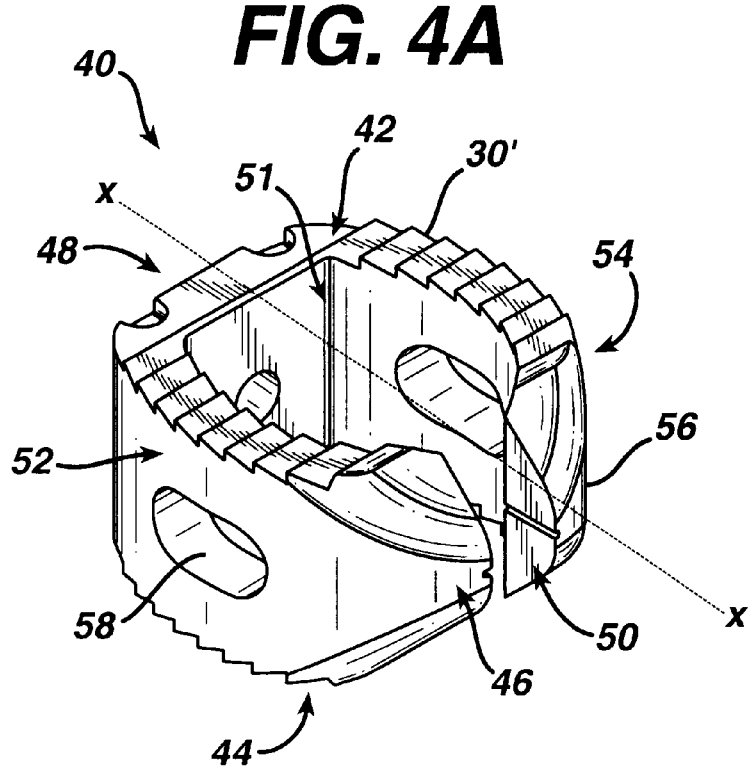
FIG. 4A is a posterior perspective view of a ring member according to one embodiment of the present invention.
Figure 4B:
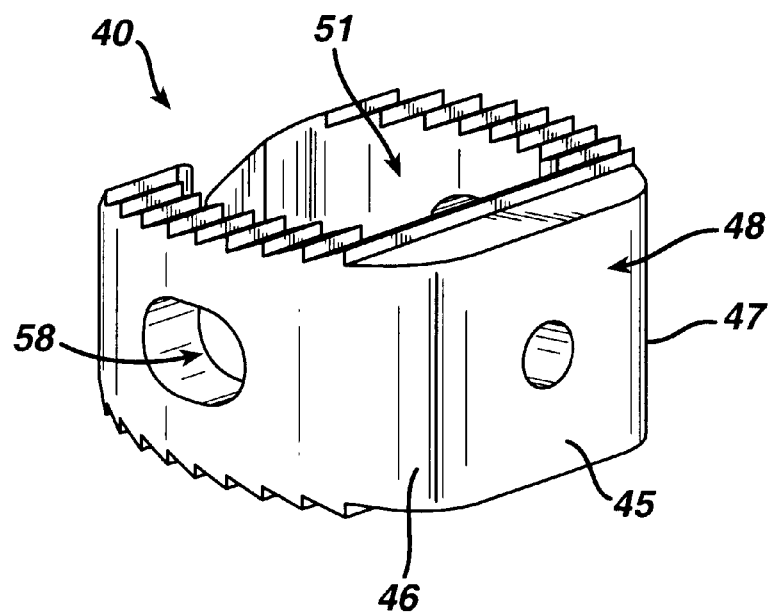
FIG. 4B is an anterior perspective view of the ring member of FIG. 4A.

The ring member 40, which is slidably matable with the ramp member 20, is shown in FIGS. 4A and 4B. In general, the ring member 40 can be a C-shaped annular body that includes superior and inferior bone contacting surfaces 42, 44, posterior and anterior sides 46, 48, and first and second transverse sides 52, 54 extending between the posterior and anterior sides 46, 48. The annular body of the ring member 40 defines a central opening 51 that is oriented in the center of the ring member 40 and extends between the superior and inferior surfaces 42, 44. The posterior side 46 of the ring member 40 includes a wall opening 50 formed by an interruption in the continuity of the annular walls of the ring member. The opening 50 is in communication with the central opening 51, and is adapted to receive the ramp member 20. The opening 50 can be formed between the first and second transverse walls 52, 54, or can be positioned at some other location on the ring member 40 depending on the surgical approach to be used. For example, where an anteriolateral surgical approach is used, the opening can be angularly positioned along one of the transverse walls 52, 54 adjacent the posterior side 46 of the ring member 20. The size of the opening 56 can be selected to conform to the width of the ramp member 20 as defined by the transverse sides 32, 34. Alternatively, the width of the opening can be slightly larger than the width of the ramp member 20.

As shown in FIG. 4B, the anterior side 48 of the ring member 40 can have a generally square or rectangular shape with rounded edges 47, and can include a flattened surface 45. The flattened surface 45 is effective to facilitate the insertion of the ring member 40 around the ramp member 20 such that an impacting device, such as a mallet or hammer, can be used to apply force to the flattened surface of the ring member 40, and thereby push the ring member 40 around the ramp 20.

The transverse walls 52, 54 of the ring member 40 extend from the anterior side 48 and can be slightly rounded to form the C-shaped ring member 40. The transverse walls 52, 54 can have any thickness, however, the walls 52, 54 should further define the opening 51 in the ring member 40. The walls 52, 54 can include one or more openings or bores 58 for receiving bone growth promoting materials, such as cancellous bone. The openings 58 can have any size and any shape, and can be positioned anywhere along the transverse walls 52, 54.

The superior and inferior surfaces 42, 44 of the ring member 40 can be parallel to each other, and can include a converging tip 56 formed along the posterior side 46 to facilitate the insertion of the ring member 40 between adjacent vertebrae. Preferably, the tip 56 possesses a substantially wedge-like or bullet-like shape, and is formed by a general convergence or curvature of the opposed superior and inferior surfaces 42, 44 towards each other. The tip 56 can extend over a region that represents a distance of about 10 to 50 percent of the anterior-posterior depth of the body 40, and can have an angle of convergence between about 10 and 25 degrees, and most preferably about 17.5 degrees with respect to the anterior-posterior axis x. As illustrated, the posterior-most portion of the tip 56 can have a generally rounded shape.

Figure 5A:
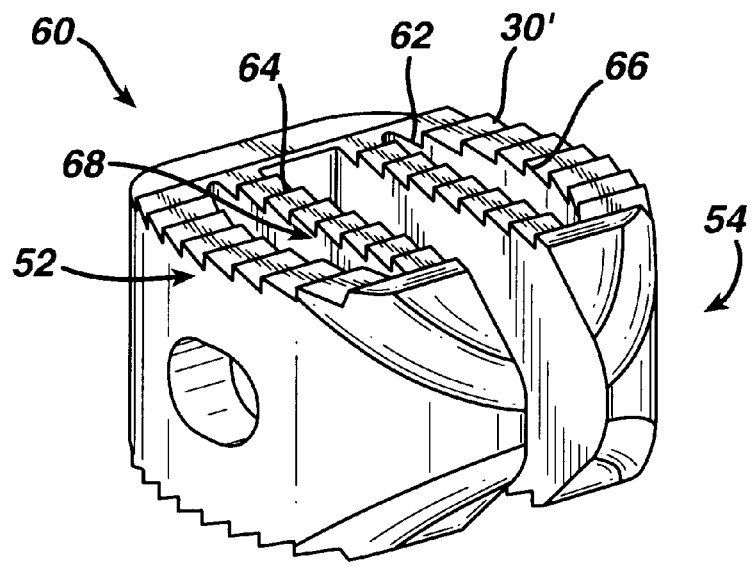
FIG. 5A is a posterior perspective view of another embodiment of a ring member according to the present invention.
Figure 5B:
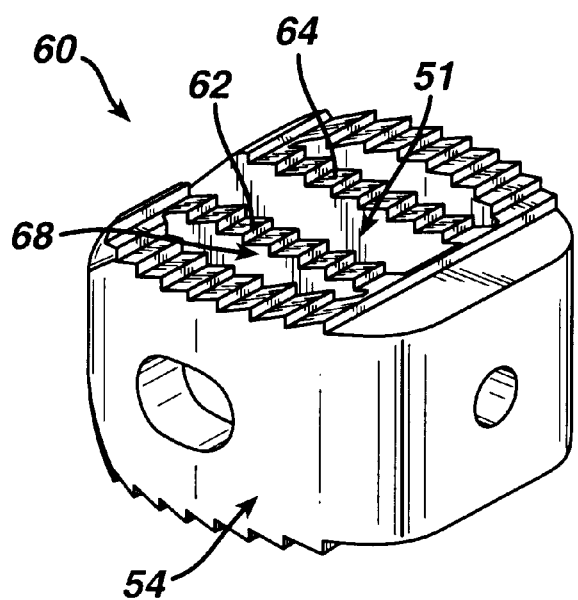
FIG. 5B is an anterior perspective view of the ring member of FIG. 5A.

The ring member according to the present invention can also include a pair of rib members 62, 64 which extend between the superior and anterior sides 46, 48, as shown in FIGS. 5A and 5B. The first and second rib members 62, 64 are parallel to each other and separate the central opening 51 and first and second bone-ingrowth openings 66, 68. The bone-ingrowth openings 66, 68 can have any shape and size, and are effective to receive bone growth promoting materials, such as cancellous bone. The rib members 63, 64 are also effective to provide additional structural integrity to the ring member 60.

The superior and inferior surfaces of the ring member according to the present invention can also optionally include a number of bone engaging surface features 30' similar in construction and purpose to the bone engaging surface features 30 described with respect to the ramp member 20. Referring to FIG. 4A, surface feature-free regions can be located along the anterior side 48 of the superior and inferior surfaces 42, 44 to facilitate grasping of the ring member 40, and on the converging tip 56 on the posterior side of the superior and inferior surfaces 42, 44 to facilitate insertion of the ring member 40 into the vertebral space.

Figure 6:
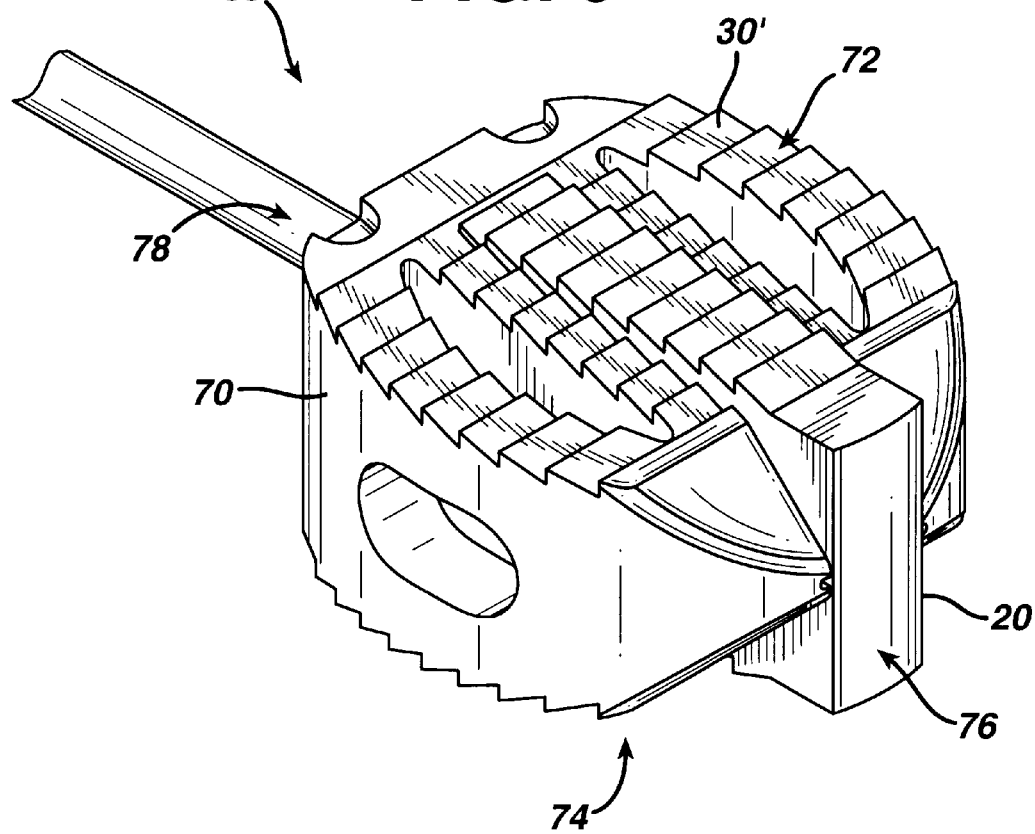
FIG. 6 is a posterior perspective view of a modular fusion cage having a ring member with sloped superior and inferior surfaces according to another embodiment of the present invention.
Figure 7A:
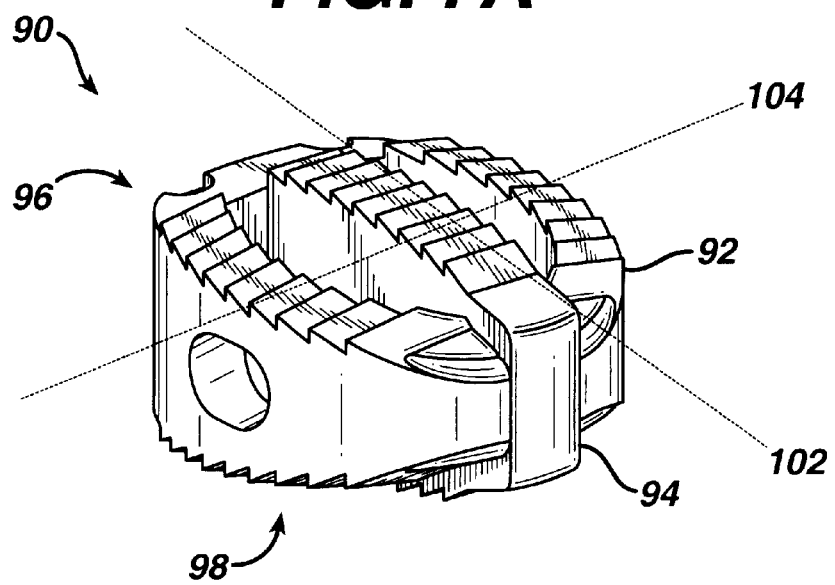
FIG. 7A is a posterior perspective view of a modular fusion cage having dome shaped superior and inferior surfaces.
Figure 7B:
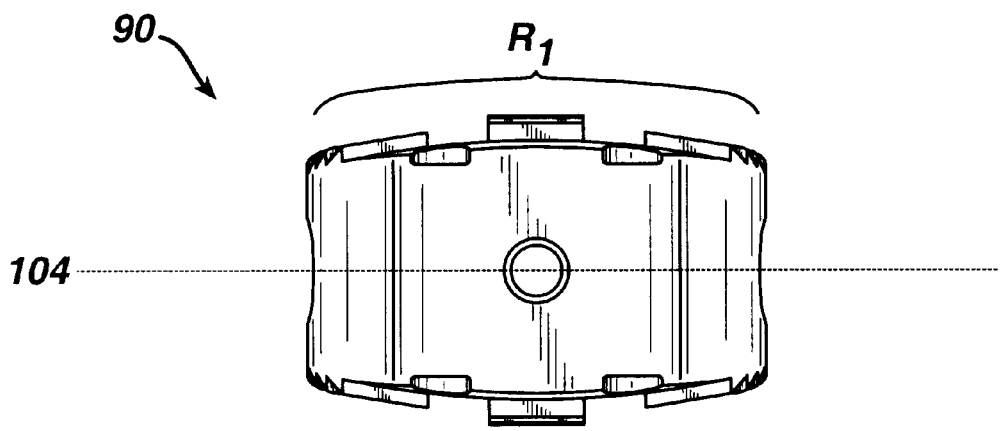
FIG. 7B is an anterior view of the modular fusion cage of FIG. 7A.
Figure 7C:
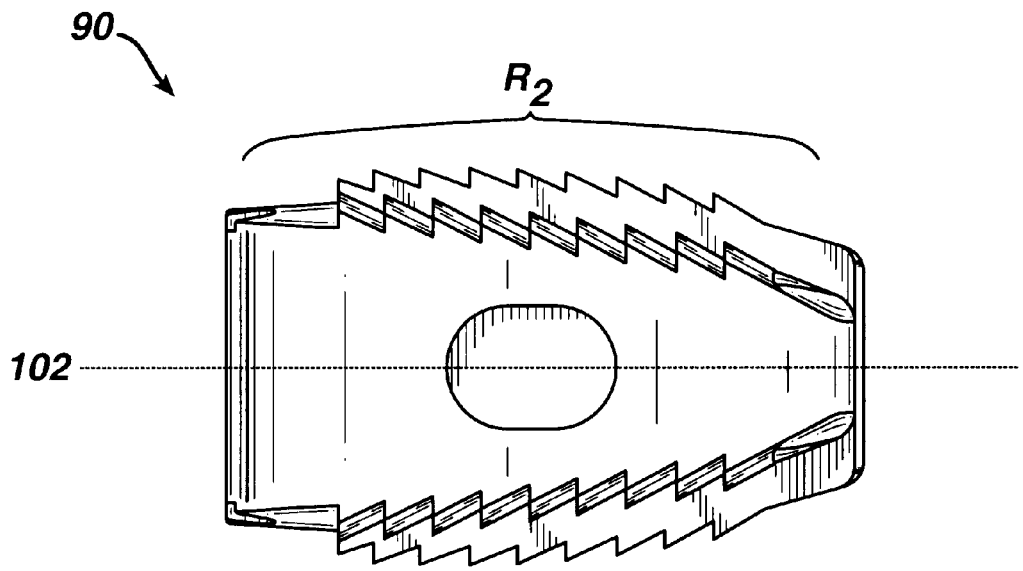
FIG. 7C is a side illustration of the modular fusion cage of FIG. 7A.

By way of non-limiting example, FIGS. 6–7C illustrate alternative embodiments of a ring member according to the present invention. A person having ordinary skill in the art will appreciate that the features illustrated herein can be formed on one or both of the ring and ramp members.

FIG. 6 illustrates a modular fusion cage 80 having assembled together a ramp member 20 and a ring member 70, similar to ring member 60 described with respect to FIGS. 5A and 5B. The ring member 70 includes sloped superior and inferior surfaces 72, 74. As shown in comparison to the ramp member 20, the incline on the superior and inferior surfaces 72, 74 extends from the posterior side 76 to the anterior side 78, thus making the thickness of the ring member 70 greater on the anterior side than on the posterior side. The degree of the incline can be determined based on the angle of the adjacent endplates of the particular vertebral bodies where the cage is to be implanted, and is preferably in the range of about 0° to 15°, and more preferably about 10°. In use, the sloped surfaces 72, 74 facilitate insertion of the ring member 70 into the vertebral space, particularly where the cage is implanted between vertebral bodies located on the lower portion of the spine. In addition.to the ring member 70 having sloped superior and inferior surfaces 72, 74, the ramp member 20 can also or alternatively include sloped superior and inferior surfaces (not shown).

FIGS. 7A–7C illustrate another embodiment of a modular fusion cage 90 having a ring member 92 and ramp member 94, each having a dome-like or convex profile on the superior and inferior surfaces 96, 98. In addition to having a dome-like profile, the ring member and ramp member 92, 94 are shown having sloped superior and inferior surfaces 96, 98.

The dome-like profile of the ring and ramp members 92, 94 is formed by a curvature located in both the sagittal and coronal planes 102, 104. FIG. 7B illustrates the radius of curvature $R_1$ in the coronal plane 104 of the superior and inferior surfaces 96, 98, and FIG. 7C illustrates the radius of curvature $R_2$ in the sagittal plane of the superior and inferior surfaces 96, 98. The radius of curvature $R_1$, $R_2$ in each plane is preferably in the range of about 50 mm to 350 mm, and is more preferably in the range of about 100 mm to 200 mm. Most preferably, the radius of curvature $R_1$, $R_2$ is about 150 mm.

In use, the modular fusion cage of the present invention can be implanted between adjacent vertebrae preferably using an anterior or anterio-lateral approach. Generally, the ramp member 20 is positioned between adjacent vertebrae in an orientation in which the transverse sides 32, 34 are in contact with the end plates of the adjacent vertebral bodies. Thereafter, the ramp member 20 is rotated 90° to enable the superior and inferior surfaces 22, 24 to contact and distract the end plates of the vertebral bodies. The modular construction of the fusion cage of the invention and its manner of installation promotes a safe and effective surgical procedure. Placement of the ramp 20 in an initial orientation in which the transverse sides 32, 34 contact the vertebral end plates can be accomplished without undue distraction of the vertebrae. Once the ramp 20 is rotated, the vertebrae are distracted only by the amount necessary to accept the fusion cage. When the ramp is properly positioned, the ring member is mated to the ramp, as explained below, without any additional distraction.

The ramp member 20 can also be inserted between adjacent vertebrae using a distractor or spreader device. Distractor and spreader devices are known in the art, and are effective for separating adjacent vertebrae, and optionally assisting with insertion of the implant. Typical distractors include two opposed blade members which are inserted between the adjacent vertebrae, and then opened to separate the vertebrae. The ramp member 20 can then be inserted into the disk space either manually, or with using an impacting device, such as a mallet.

Figure 8A:
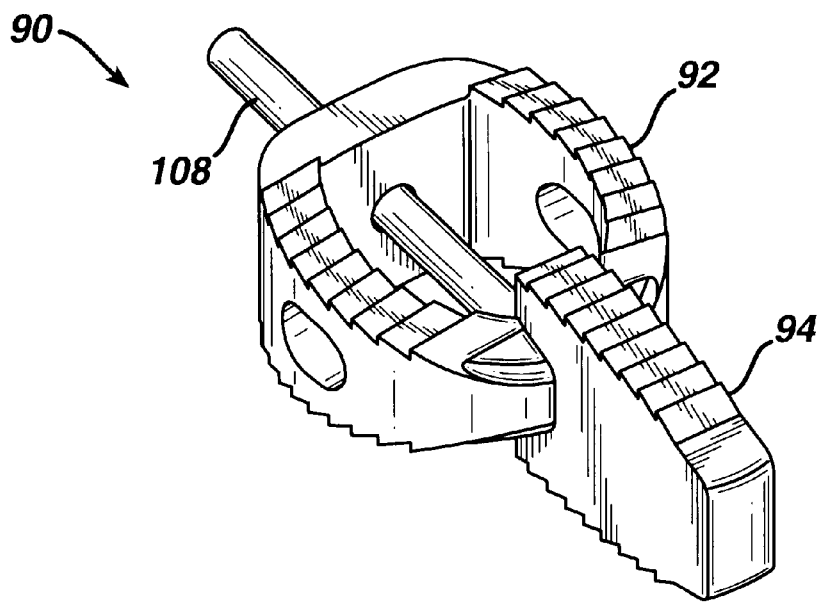
FIG. 8A is a top posterior perspective view of a partially assembled modular fusion cage having a handle mated to a ramp member according to another embodiment of the present invention.
Figure 8B:
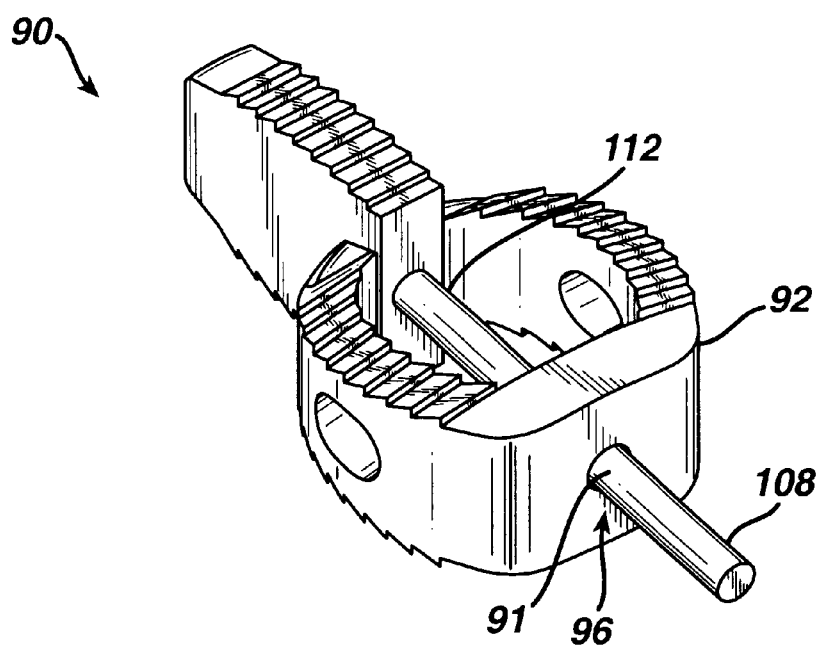
FIG. 8B is a top anterior perspective view of the modular fusion cage and handle of FIG. 8A.

By way of non-limiting example, FIGS. 8A and 8B illustrate a modular fusion cage 90, as described with respect to FIGS. 7A–7C, having a handle 108 for inserting the ramp member 94 between adjacent vertebrae, and for positioning the ring member 92 around the ramp member 94. The handle 108 can have any size and shape, and is preferably a substantially elongate rigid member having a distal end 112 removably attached to the anterior side 28 of the ramp member 94. The handle 108 can be mated to the ramp member 94 using any type of fastening element, such as, for example, threads which engage similar threads in a bore disposed in the ramp member 94, or a taper post matable with a taper bore disposed in the ramp member 94. Alternatively, the handle 108 can be formed integrally with the ramp member 94 and, once the modular fusion cage is implanted, the handle can be broken or snapped off of the ramp member 94. A person having ordinary skill in the art will readily appreciate that handle 108 can be disposed on or attached to the ramp member 94, or the ring member 92 using a variety of different techniques.

Once the ramp member 94 is positioned, the handle 108 can be removed, or alternatively, it can be used to assist with the insertion of the ring member 92 around the ramp member 94. As shown in FIG. 8B, the ring member 92 can include an opening or bore 91 disposed in the anterior side 96 for receiving the handle 108. The opening should be sized and shaped to slidably receive the handle, and should be positioned to align the ring member 92 with the ramp member 94 upon insertion of the ring member 92. The handle can be used to hold the ramp member 94 in position while an impacting device is used to force fit the ring member around the ramp member, if necessary.

The modular fusion cage according to the present invention can optionally include an alignment guide in addition to, or as an alternative to, the handle 108. By way of non-limiting example, the ramp member 20 and ring member 40 shown in FIG. 2 include an alignment guide formed from at least one tongue 12 disposed on at least one transverse side 16 of the ramp member 20, and at least one groove 14 formed along the inner side (not shown) of at least one of the transverse walls 52, 54 of the ring member 40. In use, the tongue 12 and groove 14 are aligned with one another and the ring member 40 is mated with the ramp 20 by sliding the ring member 40 over the ramp member 20. Although the fusion cage is described as having a tongue on the ramp and a groove on the ring, this arrangement can be reversed. In addition, other alignment mechanisms can be used, such as, for example, a morse-taper, dovetail, or mortise and tenon mechanism.

The tongue and groove 12, 14 can be tapered (not shown) toward the anterior side 48 to form a dovetail lock, or similar type of locking mechanism. The taper is preferably at an angle between about 0° and 5°. In use, the locking mechanism prevents the ring member 40 from sliding with respect to the ramp member 20. A person having ordinary skill in the art will appreciate that a variety of different types of locking mechanisms can be used to prevent the ring member from moving with respect to the ramp member. For example, a fastening element (not shown), such as a screw, can be inserted through opening 96 (shown in FIG. 8B) to replace the handle 108 and secure the ring member 92 to the ramp member 94.

Figure 9A:
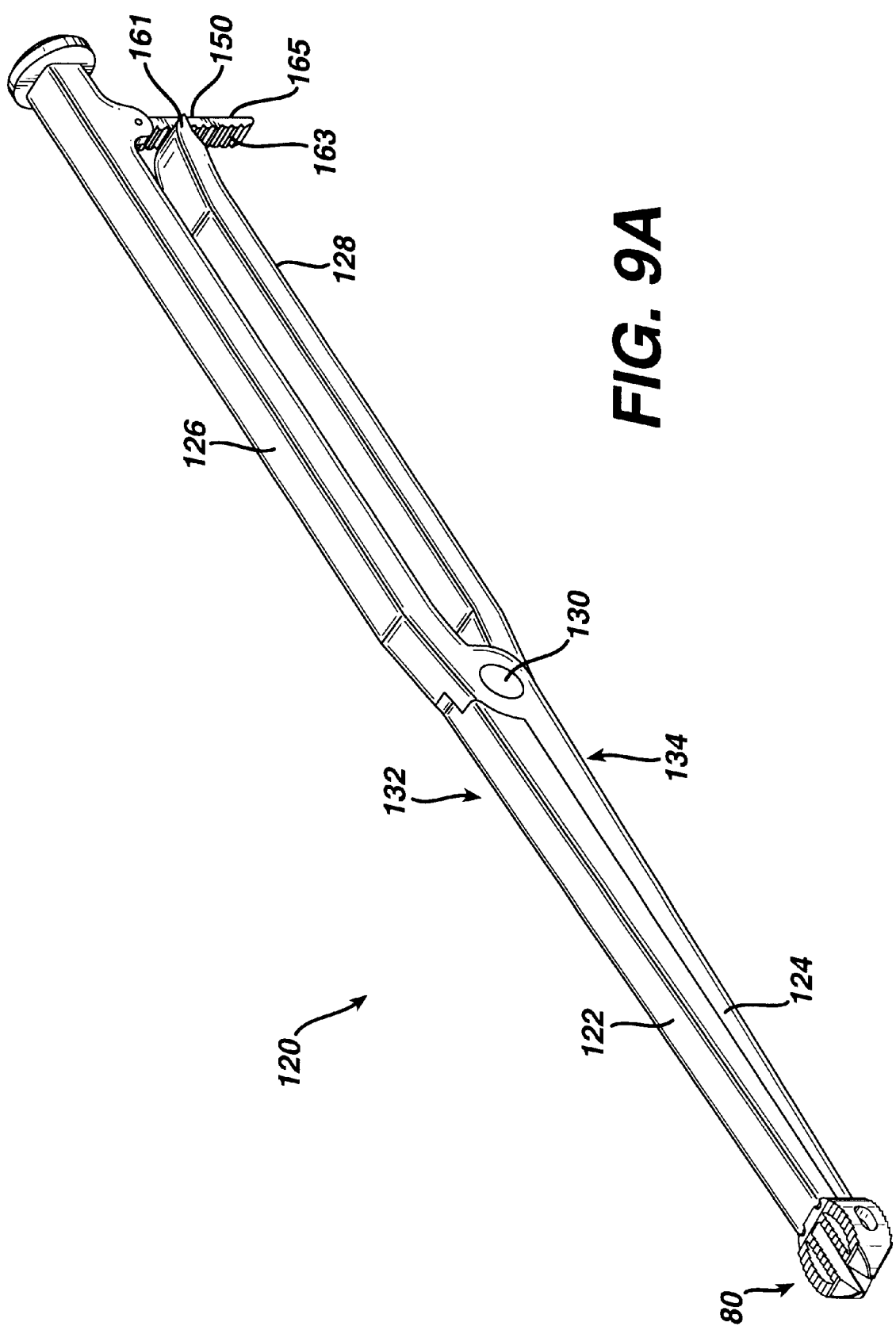
FIG. 9A is a top perspective view of a portion of an insertion tool and a ring member according to yet another embodiment of the present invention.
Figure 10:
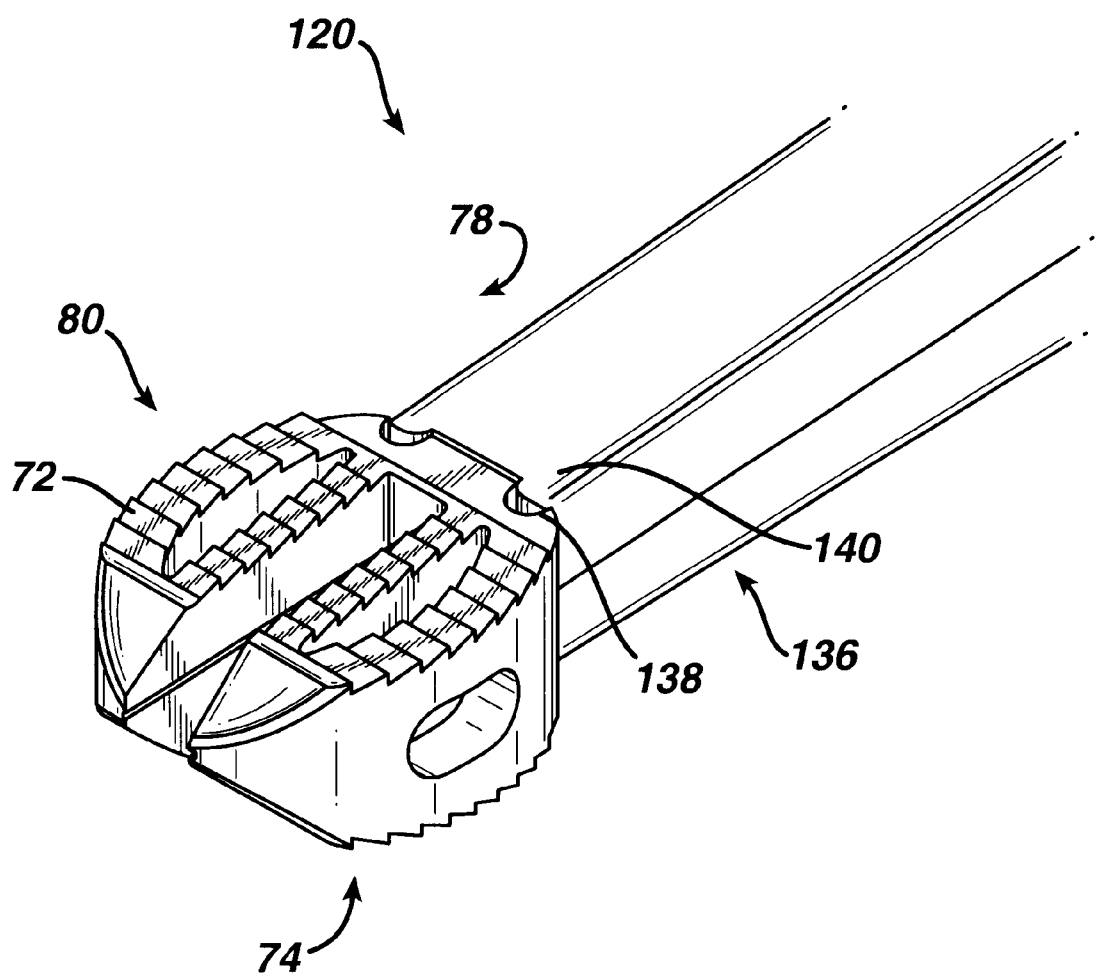
FIG. 10 is an enlarged view of the insertion tool and ring member of FIG. 9A.

As shown in FIGS. 9A and 10, the present invention also provides an insertion tool 120 which can be used to insert the ring member around the ramp member. In general, the insertion tool 120 includes two opposed grasping elements 122, 124 and two opposed handles 126, 128 mated at pivot point 130 in a scissor-like fashion. The first grasping element 122 is mated to handle 128 to form a first lever 132, and the second grasping element 124 is mated to handle 126 to form a second lever 134. A fastening element, such as a pin, screw, or similar structure can be used to mate the first and second levers 132, 134. The insertion tool 120 can optionally include a locking element 150 to prevent the first and second levers 132, 134 from moving with respect to each other. In one embodiment, the locking element 150 can be in the form of a ratchet mechanism in which a pawl 161 is disposed at a proximal end of the handle 128 and teeth 163 are formed on a lever 165 that is pivotally attached to handle 126. In another embodiment, the locking mechanism 150 can be in the form of a vise-grip 182, as shown on insertion tool 180 in FIG. 9B. Vise-grips are known in the art and typically employ a toggle mechanism (not shown) which allows for the first and second levers 132, 134 to be maintained in locking engagement with the implant 80 once a force is applied to the handle members 126, 128. The vise-grips 182 can include an adjustment screw (not shown) which must be initially adjusted to set the opening of the levers 132, 134 in relation to the implant to be grasped.

As shown in FIG. 10, the distal end 136 of each grasping element 122, 124 includes at least one engaging element 138 for mating with and grasping a ring member 80. Each engaging element 138 can be formed from an extending portion protruding from the distal end 136 of each grasping element 122, 124, and can have a shape and size adapted to fit within a groove 140 formed in the anterior side 78 of the superior and inferior surfaces 72, 74 of the ring member 80. A person having ordinary skill in the art will appreciate that ring member 80 (shown in FIG. 6) is shown for illustration purposes only, and that any ring member according to the present invention can be used with insertion tool 120.

In use, the engaging elements 138 are placed in the grooves 140 in the ring member 80, and the handles 126, 128 are squeezed together to hold the ring member 80 securely at the distal end 138 of the insertion tool 120. The locking element 150 can be engaged to lock the handles 126, 128 together and thereby hold the ring member 80. The insertion tool 120 is then manipulated to position the ring member 80 around a ramp member. The locking element 150 can then be released when it is appropriate to free the ring member 80. A person having ordinary skill in the art will appreciate that prior to insertion of the ring member 92 around the ramp member 94, the ring member 92 can be packed with a bone ingrowth promoting composition that may include, for example, cancellous bone.

The modular fusion cage of the present invention may be constructed from a variety of materials that are biocompatible and suitable for medical applications. One preferred material from which the implant can be made is a carbon fiber reinforced polymer. Other materials from which the implants can be made include metals, metal alloys, biologically compatible polymers, allograft bone, and combinations of these materials.

One of ordinary skill in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A modular fusion cage, comprising:
   a ramp member adapted to be positioned between adjacent vertebral bodies, the ramp member having superior and inferior bone contacting surfaces, and anterior and posterior sides; and
   a cage forming member having a central opening extending in a superior-inferior plane that is defined by an annular wall that is interrupted by a wall opening that is adapted to slidably receive the ramp member and that communicates with the central opening, the annular wall further having superior and inferior bone contacting surfaces, and anterior and posterior sides.

2. The modular fusion cage of claim 1, wherein the wall opening is disposed in the posterior side of the cage forming member.

3. The modular fusion cage of claim 2, wherein the cage forming member includes first and second transverse walls extending between the posterior and anterior sides.

4. The modular fusion cage of claim 3, wherein the wall opening in the posterior side of the cage forming member extends between the first and second transverse walls of the cage forming member.

5. The modular fusion cage of claim 4, wherein the ramp member includes first and second transverse sides adapted to conform to the wall opening in the posterior side of the cage forming member.

6. The modular fusion cage of claim 5, wherein at least one of the cage forming member and the ramp member includes an alignment guide that is effective to align the cage forming member and the ramp member.

7. The modular fusion cage of claim 6, wherein the alignment guide is disposed on the transverse sides of the ramp member, and on the opposed faces of the annular wall that are adjacent to the wall opening of the cage forming member.

8. The modular fusion cage of claim 6, wherein the alignment guide comprises a dovetail lock.

9. The modular fusion cage of claim 6, wherein the alignment guide comprises a tongue and groove joint.

10. The modular fusion cage of claim 5, wherein at least one of the ramp member and the cage forming member includes a locking mechanism for locking the cage forming member to the ramp member.

11. The modular fusion cage of claim 10, wherein the locking mechanism comprises a dovetail lock.

12. The modular fusion cage of claim 4, wherein the superior and inferior surfaces of the posterior side of the cage forming member define a wedge-like tip.

13. The modular fusion cage of claim 12, wherein at least a portion of the superior and inferior surfaces of at least one of the cage forming member and the ramp member include a plurality of bone-engaging surface features.

14. The modular fusion cage of claim 13, wherein the wedge-like tip is substantially free of bone engaging surface features.

15. The modular fusion cage of claim 1, wherein the ramp member has a height extending between the superior and inferior bone contacting surfaces and the height of the ramp member decreases from the anterior side to the posterior side.

16. The modular fusion cage of claim 1, wherein the cage forming member has a height extending between the superior and inferior bone contacting surfaces and the height of the cage forming member decreases from the anterior side to the posterior side.

17. The modular fusion cage of claim 16, wherein the height of the ramp member is greater than the height of the cage forming member.

18. The modular fusion cage of claim 1, wherein the superior and inferior bone contacting surfaces of the cage forming member have a convex shape in both the saggital and coronal planes.

19. The modular fusion cage of claim 1, wherein the ramp member includes a handle removably mated to the anterior side of the ramp member.

20. The modular fusion cage of claim 19, wherein the anterior side of the cage forming member includes a bore formed therein for slidably receiving the handle.

21. The modular fusion cage of claim 20, wherein the bore is adapted to receive a fastening element effective to secure the cage forming member to the ramp member.

22. The modular fusion cage of claim 1, wherein the cage forming and ramp members are made from a material selected from the group consisting of allograft bone, metals, metal alloys, carbon fiber reinforced polymers, biocompatible polymers and combinations thereof.

23. A modular fusion cage, comprising:
a substantially rectangular ramp member adapted to be positioned between adjacent vertebral bodies, the ramp member having opposed transverse sides, superior and inferior bone contacting surfaces, and anterior and posterior ends; and
a substantially annular ring-like member slidably matable with the ramp member, the ring-like member being formed of a structural wall that is interrupted by a wall opening, the ring-like member having
superior and inferior bone contacting surfaces, anterior and posterior ends, and first and second rib members extending between the posterior and anterior ends and disposed inwardly of the structural wall;
a central opening, oriented in a superior-inferior plane, and disposed between the rib members; and
first and second transverse openings, oriented in a superior inferior plane, and disposed between one of the rib members and the structural wall.

24. The modular fusion cage of claim 23, wherein the superior and inferior surfaces of the posterior side of the ring-like member define a wedge-like tip.

25. The modular fusion cage of claim 24, wherein at least a portion of the superior and inferior surfaces of at least one of the ring-like member and the ramp member include a plurality of bone engaging surface features, each bone engaging surface feature having a base integral with one of the superior and inferior surfaces.

26. The modular fusion cage of claim 25, wherein the wedge-like tip is substantially free of bone engaging surface features.

27. The modular fusion cage of claim 23, wherein at least one of the ring-like member and the ramp member includes an alignment guide that is effective to align the ring-like member with the ramp member.

28. The modular fusion cage of claim 27, wherein the alignment guide is disposed on the transverse sides of the ramp member, and on the opposed faces of the annular wall that are adjacent to the wall opening of the ring-like member.

29. The modular fusion cage of claim 23, wherein at least one of the ramp member and the ring-like member includes a locking mechanism for locking the ring member to the ramp member.

30. The modular fusion cage of claim 23, wherein the ramp member has a height extending between the superior and inferior bone contacting surfaces and the height of the ramp member decreases from the anterior side to the posterior side.

31. The modular fusion cage of claim 23, wherein the ring-like member has a height extending between the superior and inferior bone contacting surfaces and the height of the ring-like member decreases from the anterior side to the posterior side.

32. The modular fusion cage of claim 31, wherein the height of the ramp member is greater than the height of the ring-like member.

33. The modular fusion cage of claim 23, wherein the superior and inferior bone contacting surfaces of the ring-like member have a convex shape in both the saggital and coronal planes.

34. The modular fusion cage of claim 23, wherein the ramp member includes a handle removably mated to the anterior side of the ramp member.

35. The modular fusion cage of claim 34, wherein the ring-like member includes a bore formed in the anterior side of the ring-like member for slidably receiving the handle.

36. The modular fusion cage of claim 23, wherein the ring-like and ramp members are made from a material selected from the group consisting of allograft bone, metals, metal alloys, carbon fiber reinforced polymers, biocompatible polymers and combinations thereof.

37. A modular fusion cage, comprising:
a ramp member having posterior and anterior faces, superior and inferior bone contacting faces, and first and second transverse faces;
a ring member defined by an annular wall having posterior and anterior faces, superior and inferior bone contacting faces, and first and second transverse faces, the posterior face including an opening formed in the annular wall for receiving the ramp member.

38. A spinal implant system, comprising:
a modular fusion cage having
a ramp member having posterior and anterior faces, superior and inferior bone contacting faces, and first and second transverse faces, and
a ring member defined by an annular wall having posterior and anterior faces, superior and inferior bone contacting faces, and first and second transverse faces, the posterior face including an opening formed in the annular wall for receiving the ramp member, the anterior side of the superior and inferior faces further having at least one groove formed therein for receiving an insertion tool;
an insertion tool effective to grasp and manipulate the ring member relative to the ramp member, the insertion tool having
first and second opposed grasping elements movable between an open position and a closed position and matable with the at least one groove formed in each of the superior and inferior faces of the ring member, and
first and second opposed actuating members mated to the first and second grasping elements and effective to move the first and second grasping elements between the open and closed positions.

39. A method of implanting a spinal disk prosthesis, comprising:
providing a modular fusion cage having
a ramp member adapted to be positioned between adjacent vertebral bodies, the ramp member having superior and inferior bone contacting surfaces and first and second transverse sides, and
a cage forming member slidably matable with the ramp member, the cage forming member having a central opening adapted to receive the ramp member;
separating adjacent vertebrae, each vertebra having an endplate;

positioning the ramp member between the endplates of the adjacent vertebrae in an orientation in which the first and second transverse sides are in contact with the endplates;

rotating the ramp member to enable the superior and inferior surfaces to contact the endplates of the adjacent vertebrae; and sliding the cage forming member around the ramp member.

40. The method of claim 39, further comprising the step of locking the cage forming member to the ramp member.

41. A method of implanting a spinal disk prosthesis, comprising:

providing a modular fusion cage having a ramp member adapted to be positioned between adjacent vertebral bodies, and a ring member having a central opening adapted to slidably receive the ramp member;

separating adjacent vertebrae;

partially inserting the ramp member between the adjacent vertebrae;

impacting the ramp member with an impacting device to fully insert the ramp member between the adjacent vertebrae;

sliding the ring member around the ramp member.

42. The method of claim 41, further comprising the step of locking the ring member to the ramp member.

43. A method of implanting a spinal disk prosthesis, comprising:

providing a modular fusion cage having a ring member and a ramp member, the ring member including an opening for receiving the ramp member;

inserting the ramp member between adjacent vertebrae;

providing an insertion tool effective to grasp and manipulate the ring member, the insertion tool having first and second opposed grasping elements movable between an open position and a closed position and matable with the ring member;

grasping the ring member with the first and second grasping elements of the insertion tool;

manipulating the insertion tool to position the ring member around the ramp member.

* * * * *